US010379252B2

(12) United States Patent
Chen et al.

(10) Patent No.: US 10,379,252 B2
(45) Date of Patent: Aug. 13, 2019

(54) METHODS AND DEVICES FOR ESTIMATING WEIGHT OF AN OBJECT TO BE INSPECTED IN AN INSPECTION SYSTEM

(71) Applicants: Tsinghua University, Beijing (CN); NUCTECH COMPANY LIMITED, Beijing (CN)

(72) Inventors: Zhiqiang Chen, Beijing (CN); Yuanjing Li, Beijing (CN); Li Zhang, Beijing (CN); Ziran Zhao, Beijing (CN); Yaohong Liu, Beijing (CN); Juan Zheng, Beijing (CN); Jianping Gu, Beijing (CN); Chunguang Zong, Beijing (CN)

(73) Assignees: TSINGHUA UNIVERSITY, Beijing (CN); NUCTECH COMPANY LIMITED, Beijing (CN)

( * ) Notice: Subject to any disclaimer, the term of this patent is extended or adjusted under 35 U.S.C. 154(b) by 339 days.

(21) Appl. No.: 15/217,787

(22) Filed: Jul. 22, 2016

(65) Prior Publication Data

US 2017/0023697 A1    Jan. 26, 2017

(30) Foreign Application Priority Data

Jul. 22, 2015 (CN) .......................... 2015 1 0434952

(51) Int. Cl.
*G01V 5/00* (2006.01)
*G01N 23/04* (2018.01)
(Continued)

(52) U.S. Cl.
CPC ........... *G01V 5/0041* (2013.01); *G01N 23/04* (2013.01); *G01N 23/046* (2013.01); *G01N 23/06* (2013.01);
(Continued)

(58) Field of Classification Search
CPC ...... G01N 23/04; G01N 23/046; G01N 23/06; G01N 23/083; G01N 23/087; G01N 23/10; G01V 5/0016; G01V 5/0041; G01V 5/005
(Continued)

(56) References Cited

U.S. PATENT DOCUMENTS 4,926,452 A * 5/1990 Baker .................. G01N 23/043
                                                    250/358.1
5,319,547 A * 6/1994 Krug ...................... G01N 23/04
                                                    382/100
(Continued)

FOREIGN PATENT DOCUMENTS

CA        2411076 A1    12/2001
CN      101322009 A     12/2008
(Continued)

OTHER PUBLICATIONS

European Patent Application No. 16827253.2; Extended Search Report; dated Jul. 2, 2018; 10 pages.
(Continued)

*Primary Examiner* — Allen C. Ho
(74) *Attorney, Agent, or Firm* — BakerHostetler (57) ABSTRACT

Disclosed is a method and device for estimating weight of an object to be inspected in an inspection system. An effective atomic number and a high-energy gray value of the dual-energy corresponding to each pixel of the object to be inspected are obtained by a dual-energy radiation scanning. A mass-thickness value for a corresponding pixel is obtained from a pre-created mass-thickness attenuation curve by utilizing the effective atomic numbers and the high-energy gray value of the dual-energy for respective pixels. Weight information for at least a part of the object to be inspected is calculated by multiplying the mass-thickness value by the area of the pixel. Such a method may accurately calculate
(Continued)

US 10,379,252 B2

Page 2 the weight of the object to be inspected and save the cost for a conventional weighing hardware.

12 Claims, 3 Drawing Sheets

(51) Int. Cl.
    *G01N 23/046*      (2018.01)
    *G01N 23/06*      (2018.01)
    *G01N 23/083*      (2018.01)
    *G01N 23/087*      (2018.01)
    *G01N 23/10*      (2018.01)
    *G01V 5/12*      (2006.01)

(52) U.S. Cl.
    CPC ......... *G01N 23/083* (2013.01); *G01N 23/087* (2013.01); *G01N 23/10* (2013.01); *G01V 5/005* (2013.01); *G01V 5/0016* (2013.01); *G01V 5/12* (2013.01)

(58) Field of Classification Search
    USPC ........ 378/5, 16, 51, 53–57, 98.9, 98.11, 207
    See application file for complete search history.

(56) References Cited

U.S. PATENT DOCUMENTS

| | | | | |
|---|---|---|---|---|
| 5,335,260 A * | 8/1994 | Arnold | A61B 6/505 |
| | | | 378/18 |
| 5,479,023 A * | 12/1995 | Bartle | G01V 5/0033 |
| | | | 250/359.1 |
| 5,481,584 A * | 1/1996 | Tang | G01N 23/06 |
| | | | 378/53 |
| 5,768,334 A * | 6/1998 | Maitrejean | G01N 23/04 |
| | | | 378/53 |
| 5,917,877 A * | 6/1999 | Chiabrera | A61B 6/482 |
| | | | 378/207 |
| 6,018,562 A * | 1/2000 | Willson | G01N 23/087 |
| | | | 378/57 |
| 6,064,716 A * | 5/2000 | Siffert | A61B 6/482 |
| | | | 378/207 |
| 6,148,057 A * | 11/2000 | Urchuk | A61B 6/583 |
| | | | 378/18 |
| 6,173,038 B1 * | 1/2001 | Siffert | A61B 6/482 |
| | | | 378/174 |
| 6,201,850 B1 * | 3/2001 | Heumann | G01B 15/025 |
| | | | 378/22 |
| 6,226,352 B1 * | 5/2001 | Salb | A61B 6/4035 |
| | | | 378/143 |
| 6,231,231 B1 * | 5/2001 | Farrokhnia | A61B 6/583 |
| | | | 378/204 |
| 6,285,740 B1 * | 9/2001 | Seely | H05G 1/20 |
| | | | 250/367 |
| 6,315,447 B1 * | 11/2001 | Nord | A61B 6/482 |
| | | | 378/18 |
| 6,347,131 B1 * | 2/2002 | Gusterson | G01B 15/00 |
| | | | 378/51 |
| 6,516,045 B2 * | 2/2003 | Shepherd | A61B 6/502 |
| | | | 378/132 |
| 6,567,496 B1 * | 5/2003 | Sychev | G01N 23/04 |
| | | | 378/57 |
| 6,570,955 B1 * | 5/2003 | Siffert | A61B 6/482 |
| | | | 378/207 |
| 6,574,302 B2 * | 6/2003 | Adriaansz | A61B 6/032 |
| | | | 378/18 |
| 6,632,020 B2 * | 10/2003 | Kaufhold | A61B 6/482 |
| | | | 378/207 |
| 6,674,835 B2 * | 1/2004 | Kaufhold | A61B 5/4869 |
| | | | 378/207 |
| 6,678,396 B2 * | 1/2004 | Bartle | G01N 33/12 |
| | | | 382/110 |
| 6,694,047 B1 * | 2/2004 | Farrokhnia | A61B 6/583 |
| | | | 378/163 |
| 6,816,571 B2 * | 11/2004 | Bijjani | G01N 23/046 |
| | | | 378/57 |
| 6,824,309 B2 * | 11/2004 | Robert-Coutant | A61B 6/583 |
| | | | 378/207 |
| 7,164,749 B2 * | 1/2007 | Schrock | G01N 23/06 |
| | | | 378/53 |
| 7,215,732 B2 * | 5/2007 | Yin | G06T 11/005 |
| | | | 378/5 |
| 7,286,638 B2 * | 10/2007 | Ledoux | G01N 23/04 |
| | | | 378/57 |
| 7,366,282 B2 * | 4/2008 | Peschmann | G01N 23/04 |
| | | | 378/46 |
| 7,369,642 B2 * | 5/2008 | Eilbert | G01N 23/04 |
| | | | 378/57 |
| 7,480,363 B2 * | 1/2009 | Lasiuk | G01B 15/025 |
| | | | 378/54 |
| 7,580,505 B2 * | 8/2009 | Kang | A61B 6/4241 |
| | | | 378/54 |
| 7,583,779 B2 * | 9/2009 | Tkaczyk | A61B 6/032 |
| | | | 378/4 |
| 7,595,489 B2 * | 9/2009 | Statham | G01N 23/22 |
| | | | 250/307 |
| 7,606,349 B2 * | 10/2009 | Oreper | G01V 5/005 |
| | | | 378/137 |
| 7,646,851 B2 * | 1/2010 | Liu | G01N 23/087 |
| | | | 378/119 |
| 7,702,075 B2 * | 4/2010 | Wang | G01N 23/087 |
| | | | 378/158 |
| 7,724,865 B2 * | 5/2010 | Wu | A61B 6/032 |
| | | | 378/4 |
| 7,746,976 B2 * | 6/2010 | Huo | A61B 6/4233 |
| | | | 378/53 |
| 7,773,725 B2 * | 8/2010 | Gordon, III | G01N 23/18 |
| | | | 378/53 |
| 7,809,103 B2 * | 10/2010 | Du | G01N 23/09 |
| | | | 378/53 |
| 7,819,581 B2 * | 10/2010 | Srinivasan | G01T 7/005 |
| | | | 378/19 |
| 7,831,012 B2 * | 11/2010 | Foland | G01N 23/04 |
| | | | 378/57 |
| 7,869,566 B2 | 1/2011 | Edic et al. | |
| 7,881,424 B2 * | 2/2011 | Zhang | G01T 7/005 |
| | | | 378/5 |
| 7,924,978 B2 | 4/2011 | Harding | |
| 7,965,816 B2 * | 6/2011 | Kravis | G01V 5/0025 |
| | | | 378/57 |
| 8,027,429 B2 * | 9/2011 | Hu | G01N 23/04 |
| | | | 378/207 |
| 8,068,656 B2 * | 11/2011 | Hirose | G01N 23/04 |
| | | | 382/132 |
| 8,077,827 B2 * | 12/2011 | Perng | G01B 15/025 |
| | | | 378/207 |
| 8,094,874 B2 * | 1/2012 | Dugan | G06K 9/6263 |
| | | | 378/57 |
| 8,194,953 B2 * | 6/2012 | Xie | G01N 23/04 |
| | | | 378/41 |
| 8,218,837 B2 * | 7/2012 | Wu | A61B 6/032 |
| | | | 382/128 |
| 8,290,230 B2 * | 10/2012 | Chen | G01N 23/04 |
| | | | 378/51 |
| 8,315,352 B2 * | 11/2012 | Wu | A61B 6/032 |
| | | | 378/18 |
| 8,374,310 B2 * | 2/2013 | Kang | H05H 6/00 |
| | | | 378/57 |
| 8,401,270 B2 * | 3/2013 | Eilbert | G01V 5/0041 |
| | | | 250/306 |
| 8,406,375 B2 * | 3/2013 | Yang | G01V 5/0016 |
| | | | 378/62 |
| 8,633,823 B2 * | 1/2014 | Armistead, Jr. | G06K 9/00 |
| | | | 250/308 |
| 8,858,076 B2 * | 10/2014 | Quintana | G21K 1/10 |
| | | | 378/18 |
| 8,953,741 B2 * | 2/2015 | Yi | G01N 23/083 |
| | | | 378/45 |
| 9,113,839 B2 * | 8/2015 | Morton | A61B 6/032 |
| 9,423,363 B2 * | 8/2016 | Radley | G01N 23/087 |

(56) References Cited

U.S. PATENT DOCUMENTS

| | | | |
|---|---|---|---|
| 9,448,326 B2* | 9/2016 | Radley | G01N 23/087 |
| 9,459,218 B2* | 10/2016 | Radley | G01N 23/087 |
| 9,464,997 B2* | 10/2016 | Li | G01T 1/22 |
| 9,945,714 B1* | 4/2018 | Hartwig | G01G 9/005 |
| 10,074,166 B2* | 9/2018 | Kang | G06T 7/0004 |
| 10,089,956 B2* | 10/2018 | Awad | G06T 5/009 |
| 2003/0147489 A1 | 8/2003 | Bijjani et al. | |
| 2008/0298544 A1* | 12/2008 | Dugan | G01N 23/06 378/53 |
| 2009/0052762 A1 | 2/2009 | Dugan et al. | |
| 2012/0140884 A1 | 6/2012 | Iwakiri et al. | |
| 2015/0189239 A1 | 7/2015 | Zhao et al. | |

FOREIGN PATENT DOCUMENTS

| | | |
|---|---|---|
| CN | 102435621 A | 5/2012 |
| CN | 102590234 A | 7/2012 |
| CN | 104254769 A | 12/2014 |
| WO | WO 2006/010056 A2 | 1/2006 |

OTHER PUBLICATIONS

Iran Patent Application No. 13965014003007671; Office Action; dated Feb. 6, 2019; 12 pages.

* cited by examiner

METHODS AND DEVICES FOR ESTIMATING WEIGHT OF AN OBJECT TO BE INSPECTED IN AN INSPECTION SYSTEM

CROSS-REFERENCE TO RELATED APPLICATION(S)

This application claims priority to the Chinese Patent Application No. 201510434952.9, filed on Jul. 22, 2015, entitled "METHODS AND DEVICES FOR ESTIMATING WEIGHT OF AN OBJECT TO BE INSPECTED IN AN INSPECTION SYSTEM" which is incorporated herein by reference in its entirety.

TECHNICAL FIELD

The present disclosure relates to the field of inspection, and in particular, to methods and devices for calculating weight of an object to be inspected based on radiography.

BACKGROUND

Security Inspection is very important in the field of counter terrorism, combating drug trafficking, combatting smuggling, or the like. After 911 in US, security inspection in public places, such as airports, railway stations, is drawing more attention than ever. With the deepening of combating drug trafficking and smuggling, requirements of checking containers, baggage, or the like become increasingly demanding.

The mainstream of the existing inspection systems is a radiation imaging system of which a dual-energy radiographic system is most popular, and an effective atomic number information that may be acquired by such a system (i.e. a material property that is undoubtedly a key feature of an object to be inspected) can facilitate an image inspector in quickly identifying a security level of an object to be inspected. In addition, weight is also one of the key features of an object to be inspected, and in the past, weight of an object to be inspected is usually acquired by an imaging system with a piece of weighing hardware incorporated therein, for example, a small inspection device with a weighing sensor or a small electronic scale incorporated therein or a large inspection device with a weighbridge incorporated therein. This results in a complex and cumbersome system.

SUMMARY

In view of the one or more problems in the prior art, methods and devices for calculating weight of an object to be inspected based on radiography is proposed. In this way, not only a sufficiently accurate weight information is acquired, but also cost for a conventional weighing hardware is saved.

According to an aspect of the present disclosure, a method of estimating a weight of an object to be inspected in an inspection system is proposed. The method includes: obtaining an effective atomic number and a high-energy gray value of the dual-energy corresponding to each pixel of an object to be inspected by a dual-energy radiation scanning; obtaining a mass-thickness value for a corresponding pixel from a pre-created mass-thickness attenuation curve by utilizing the effective atomic number and the dual-energy high-energy gray value for respective pixels; and calculating weight information for at least a part of the object to be inspected by multiplying the mass-thickness value by an area of the pixel.

Preferably, the method further includes: estimating a physical dimension corresponding to each pixel on an image of the object to be inspected in a direction in which detectors are arranged, based on a pitch between detector pixels, a distance between a X-ray source and the detectors, and a distance between the X-ray source and the object to be inspected; acquiring a pixel physical dimension in a scanning direction based on a scanning speed and an acquiring frequency of the detectors; and obtaining an area of each pixel by multiplying the physical dimension in the direction in which the detectors are arranged by the pixel physical dimension in the scanning direction.

Preferably, the method further includes: creating the pre-created mass-thickness attenuation curve by: utilizing different types of calibration material blocks with known thicknesses to acquire a relationship curve among a X-ray attenuation coefficient, the effective atomic number, and the mass-thickness value, as the pre-created mass-thickness attenuation curve.

Preferably, obtaining a mass-thickness value for a corresponding pixel comprises acquiring the mass-thickness value corresponding to both of the effective atomic number and the high-energy gray value of the dual-energy by linear interpolation.

Preferably, calculating weight information for at least a part of the object to be inspected comprises acquiring the weight information for a region of interest by accumulating weights of pixels within the region interest when information of region of interest selected by a user is received.

According to another aspect of the present disclosure, a device for estimating a weight of an object to be inspected in an inspection system is proposed. The device includes: one or more processors; and a memory connected to the one or more processors and having one or more programs stored therein, which, when executed by the one or more processors, cause the one or more processors to be configured to: obtain an effective atomic number and the high-energy gray value of the dual-energy corresponding to each pixel of an object to be inspected by a dual-energy radiation scanning; obtain a mass-thickness value for a corresponding pixel from a pre-created mass-thickness attenuation curve by utilizing the effective atomic number and the dual-energy high-energy gray value for respective pixels; and calculate weight information for at least a part of the object to be inspected by multiplying the mass-thickness value by an area of the pixel.

According to yet another aspect of the present disclosure, a method of estimating a weight of an object to be inspected in an inspection system is proposed. The method includes: obtaining a grayscale feature value corresponding to each pixel of an object to be inspected by a single-energy radiation scanning; obtaining a mass-thickness value for a corresponding pixel from a pre-created mass-thickness attenuation curve by utilizing the grayscale feature value for respective pixels; and calculating weight information for at least a part of the object to be inspected by multiplying the mass-thickness value by an area of the pixel.

Preferably, the method further includes: estimating a physical dimension corresponding to each pixel on an image of the object to be inspected in a direction in which detectors are arranged, based on a pitch between detector pixels, a distance between a X-ray source and the detectors, and a distance between the X-ray source and the object to be inspected; obtaining a pixel physical dimension in a scanning direction based on a scanning speed and an acquiring frequency of the detectors; and obtaining an area of each pixel by multiplying the physical dimension in the direction in which the detectors are arranged by the pixel physical dimension in the scanning direction.

Preferably, the method further includes: creating the pre-created mass-thickness attenuation curve by: utilizing calibration material blocks with known thicknesses to acquire a relationship curve between a X-ray attenuation coefficient and the mass-thickness value, as the pre-created mass-thickness attenuation curve.

Preferably, the method further includes: selecting aluminum as a calibration material block to acquire the pre-created mass-thickness attenuation curve.

According to yet another aspect of the present disclosure, a device for estimating a weight of an object to be inspected in an inspection system is proposed. The device includes one or more processors; and a memory connected to the one or more processors and having one or more programs stored therein, which, when executed by the one or more processors, cause the one or more processors to be configured to: obtain a grayscale feature value corresponding to each pixel of an object to be inspected by a single-energy radiation scanning; obtain a mass-thickness value for a corresponding pixel from a pre-created mass-thickness attenuation curve by utilizing the grayscale feature value for respective pixels; and calculate weight information for at least a part of the object to be inspected by multiplying the mass-thickness value by an area of the pixel.

With the above solutions, the weight of the object to be inspected is calculated without weighing hardware of the inspection system, such that the structure of the inspection system becomes simpler and sufficiently accurate weight information can be acquired, thereby facilitating the image inspector in inspection.

BRIEF DESCRIPTION OF THE DRAWINGS

To understand the present disclosure in a better way, a detailed description of the present disclosure will be given with reference to the following drawings, in which.

DETAILED DESCRIPTION

Specific embodiments of the present disclosure will be described in detail below and please note that the embodiments described herein are used for the purpose of exemplification rather than limitation of the present disclosure. Hereinafter, to provide a thorough understanding of the present disclosure, numerous specific details are set forth. However, it would be obvious for one ordinarily skilled in the art that the present disclosure can be practiced without these specific details. In other examples, known structures, materials, or methods are not described in detail to avoid any possible obfuscation of the present disclosure.

In the radiation imaging principle, the most essential formula is $I=I_0 \exp(-\mu t)$, that is, current intensity of a single-energy X-ray beam is attenuated exponentially with thickness of absorbing substance where $I_0$ denotes the total number of photons before the attenuation, I denotes the number of photons after the attenuation, t denotes the mass-thickness which is the product of the thickness and density, $\mu$ denotes the mass attenuation coefficient which is a function of the energy E and the atomic number Z and which characterizes the attributes of materials.

A dual-energy inspection system utilizes two X-ray with different energy spectrums to penetrate an object to be inspected, and the effective atomic number information for materials of the object to be inspected can be obtained by utilizing the difference between their output signals. Based on the value of the effective atomic number, they are divided into four categories, i.e., organics, mixture, inorganics, and heavy metal, which are colored with orange, green, blue, and purple, respectively, such that the image inspector can be provided with properties of the object to be inspected in a visualized manner, such as a color image. In a legacy dual-energy X-ray imaging system, only important information such as properties of material is calculated and provided to the image inspector, that is, the characterization of $\mu$ in the above formula. According to an embodiment of the present disclosure, the mass-thickness t is resolved during this process, and dimensions of each pixel are obtained based on the system geometry to acquire the area of the pixels. The product of the mass-thickness and the area is calculated to acquire the weight information of the object to be inspected.

Figure 1:
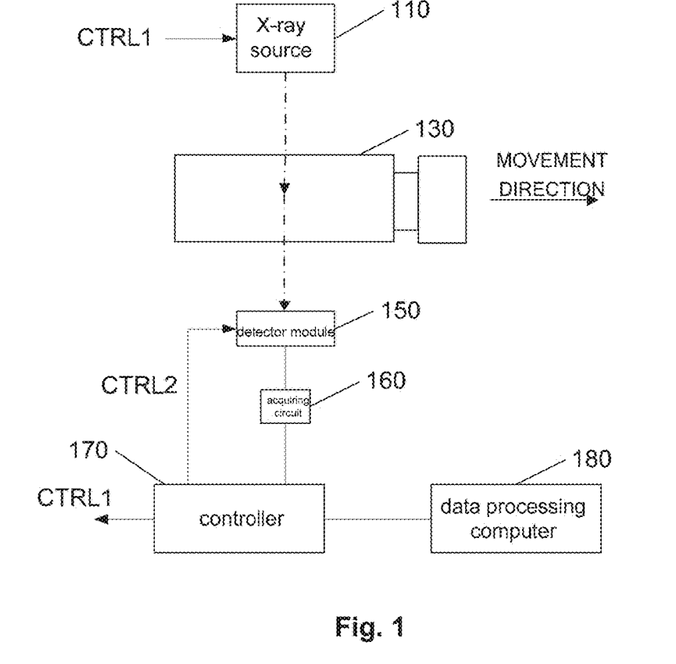
FIG. 1 is a diagram showing a dual-energy X-ray DR imaging system according to an embodiment of the present disclosure.

FIG. 1 is a diagram showing a dual-energy X-ray system according to an embodiment of the present disclosure. As shown in FIG. 1, the dual-energy X-ray system comprises an X-ray source 110, a detector module 150, an acquiring circuit 160, a controller 170, and a data processing computer 180, among others. The X-ray source 110 comprises one or more X-ray generator for performing a dual-energy scanning. The plurality of X-ray generators are distributed on one or more planes which intersect with the travelling direction of an object to be inspected 130.

As shown in FIG. 1, the object to be inspected 130 (such as a container lorry) passes through the scanning area between the X-ray source 110 and the detector module 150. In some embodiments, the detector module 150 and the acquiring circuit 160 may be, for example, a detector-and-data-acquiring unit with an integrated modular structure, such as a multiple-row detector, for detecting X-ray transmitted through the object to be inspected 130 such that analog signals are acquired and converted into digital signals, thereby outputting X-ray projection data of the object to be inspected 130. For example, a row of detectors are arranged for high-energy X-ray and another row of detectors are arranged for low-energy X-ray, or a same row of detectors are used in a time division manner for high-energy and low energy X-ray. The controller 170 is used for controlling various parts of the whole dual-energy X-ray system to operate synchronously. The data processing computer 180 is used for processing the data acquired by the acquiring circuit 160, processing and reconstructing the data, and outputting the result.

According to this embodiment, the detector module 150 and the acquiring circuit 160 are used for acquiring transmission data of the object to be inspected 130. The acquiring circuit 160 comprises a data amplification shaping circuit which may operate in a (current) integration manner or a pulse (courting) manner. A data output cable of the acquiring circuit 160 is coupled to the controller 170 and the data processing computer 180, and stores the acquired data into the data processing computer 180 based on a trigger command.

In some embodiments, the detector module 150 comprises multiple detecting units which receive the X-ray transmitted through the object to be inspected 130. The acquiring circuit 160 is coupled to the detector module 150 and converts the signals generated by the detector module 150 into the detection data. The controller 170 is coupled to the X-ray source 110 via a control line CTRL1, to the detector module 150 via a control line CTRL2, and to the acquiring circuit 160. The controller 170 controls at least two of the one or more X-ray generators in the X-ray source 110 to generate X-ray with different energy which are then emitted and pass through the object to be inspected 130 as the object to be inspected 130 moves. In addition, the controller 170 controls the detector module 150 and the acquiring circuit 160 to acquire detection data corresponding to the X-ray generators with at least two energy, respectively. The data processing computer 180 reconstructs the image of the object to be inspected 130 based on the detection data, and/or acquires the weight information for at least a part of the object to be inspected 130 based on processing of the detection data.

Figure 2:
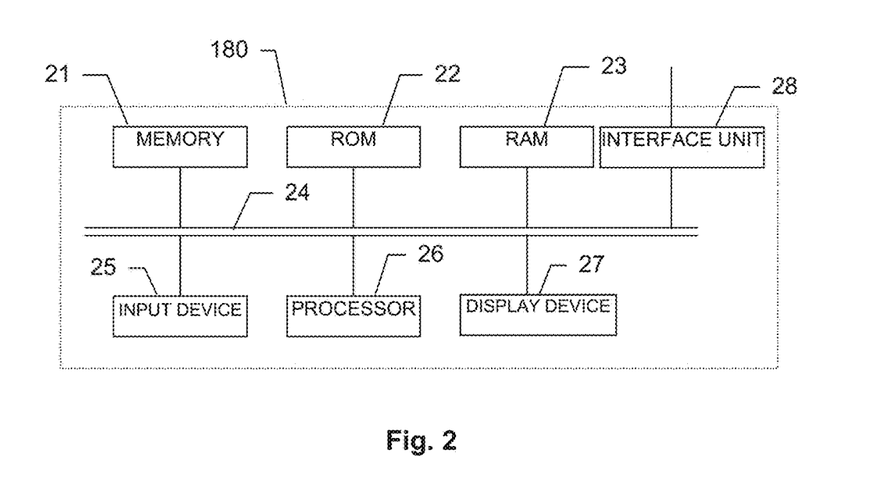
FIG. 2 is a diagram showing an internal structure of a computer for image processing in the embodiment shown in FIG. 1.

FIG. 2 is a block diagram showing the structure of the data processing computer 180 as shown in FIG. 1. As shown in FIG. 2, the data acquired by the acquiring circuit 160 is stored into a memory 21 via an interface unit 28 and an internal bus 24. Configuration information and programs for the data processing computer 180 are stored in a Read-Only Memory (ROM) 22. A Random Access Memory (RAM) 23 is used for temporarily storing various data during the operation of a processor 26. In addition, computer programs for data processing are also stored in the memory 21. The internal bus 24 connects the above memory 21, ROM 22, RAM 23, an input device 25, the processor 26, a display device 27, and the interface unit 28.

After an operation command is input by a user via the input device 25, such as a keyboard, a mouse, etc., the code instructions of the computer program instructs the processor 26 to perform a predetermined data reconstruction algorithm. After the result of the data processing is acquired, it will be displayed on the display device 27, such as an LCD display, or output directly in a hardcopy form, such as printing.

For example, the X-ray source 110 may be a radioisotope (such as, Cobalt-60), or a low-energy X-ray or high-energy X-ray accelerator.

For example, in terms of material, the detector module 150 may be a gas detector, a scintillator detector, or a solid detector, etc., and in terms of array arrangement, the detector module 150 may be a single-row, double-row, or multiple-row detector array, or a single-layer detector or a double-layer detector, or the like.

Although it is described above that the object to be inspected 130, such as a container lorry, passes through the checking area on its own, one skilled in the art could contemplate that the object to be inspected 130 can be placed on a transfer mechanism, such as a belt, and pass through the scanning area. Further, it is also possible for the object to be inspected 130 to stay still and for the X-ray source 110 and the detector module 150 to move and accomplish the scanning process.

One embodiment of the present disclosure is based on the dual-energy X-ray system. It calculates the mass-thickness, obtains dimensions of each pixel based on the dual-energy X-ray system geometry, and in turn obtains the area of the pixels. The product of the mass-thickness and the area is calculated to acquire the weight information of the object to be inspected 130. In an embodiment of the present disclosure, a calibration material block is first used for calibration to acquire a relationship curve among the dual-energy X-ray attenuation coefficient, the effective atomic number, and the mass-thickness, i.e., the mass-thickness curve. The density of at least a part of the object to be inspected 130 is then calculated by using the determined mass-thickness curve during a practical inspection process, and then its weight information is determined in conjunction with the geometry of the object to be inspected 130.

Figure 3:
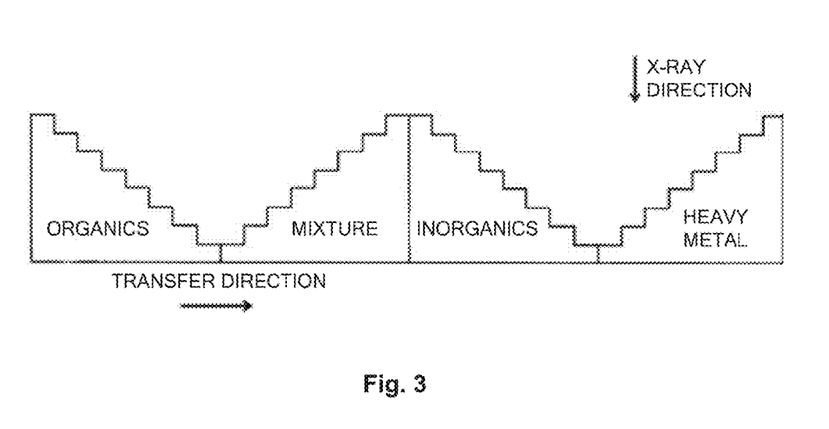
FIG. 3 is a diagram showing a calibration material block used in an inspection system according to an embodiment of the present disclosure.

FIG. 3 is a diagram showing a calibration material block (calibration device) used in an inspection system according to an embodiment of the present disclosure. As shown in FIG. 3, a general calibration device contains four types of typical materials, i.e., organics, mixtures, inorganics, and heavy metal, each of which has several steps from thinner to thicker. The X-ray pass through the steps perpendicularly.

The transfer direction is perpendicular to the X-ray direction, such that the calibration device is moved relative to the dual-energy X-ray system. When the object to be inspected 130 is scanned, the calibration device is removed to not block the ray beam, the X-ray source 110 emits the X-ray beam, positions of the dual-energy X-ray system and the object to be inspected 130 are moved relatively until the scanning of the object to be inspected 130 is done and the process ends. When the dual-energy X-ray system enters the automatic calibration process, the object to be inspected 130 is removed to not block the X-ray beam, the X-ray source 110 emits the X-ray beam, the calibration steps block the X-ray beam one step by one step, and the process ends after all the step data are acquired.

The calibration material block as shown in FIG. 3 is used to obtain a relationship curve between the dual-energy X-ray attenuation coefficient and the effective atomic number, that is, acquire a classification curve. The calibration process for obtaining the classification curve is introduced briefly below: first, the calibration device is designed such that the calibration device comprises four types of typical materials, graphite (C, Z=6), aluminum (Al, Z=13), iron (Fe, Z=26), and lead (Pb, Z=82), which represent organics, mixture, inorganics, and heavy metal, respectively, each of which has several steps from thinner to thicker. An average data for each step are calculated and then four curves are fitted.

After that, on the basis of the classification curve, a relationship curve among the dual-energy X-ray attenuation coefficient, the effective atomic number, and the mass-thickness is acquired, i.e., the mass-thickness attenuation curve. The details are given below:

First, a calibration device for acquiring the classification curve or a calibration device achieved based on the requirements on the real system design may be used. This device comprises four types of typical materials, i.e., graphite (C, Z=6), aluminum (Al, Z=13), iron (Fe, Z=26), and lead (Pb, Z=82), which represent organics, mixture, inorganics, and heavy metal, respectively, each of which has several steps from thinner to thicker.

The X-ray source 110 emits the X-ray beam in a dual-energy mode, and the dual-energy X-ray system enters the automatic calibration process. When the mechanical transfer sub-system locates the positions of each step, i.e., the X-ray passes through a certain step perpendicularly, the software acquiring sub-system acquires several rows of dual-energy transmission images. After the completion of the acquiring, the acquiring ends and the mechanical transfer system locates the next step, and the software acquiring sub-system starts the acquiring. This process loops until the dual-energy transmission images for all the steps are acquired.

The high-energy of dual-energy statistics data $-\ln(I/I_0)$ for each step is calculated, where $I_0$ is the detector data in the case where the high-energy X-ray is not blocked by the object to be inspected when the X-ray source 110 emits the X-ray beam, i.e., the data for air, I is the attenuated data in the case where the high-energy X-ray transmits through the object to be inspected 130 when the X-ray source 110 emits the X-ray beam. Since several rows of data are acquired during the acquiring, both of the above two kinds of data are the average of the several rows of data. Here only high-energy data is used and low-energy data is not used because the high-energy X-ray has high energy and strong penetration and it may acquire a X-ray attenuation value under a greater mass-thickness. However, in other embodiments, the dual-energy low-energy data or a fusion data generated based on the high-energy data and the low-energy data may also be used.

When the calibration device is designed, the mass-thickness of each step is known. Therefore, a relationship between the above statistics data and the mass-thickness can be acquired. With the statistics data as the abscissa and the mass-thickness value as the ordinate, the mass-thickness attenuation curve for 4 types of typical materials is fitted. The fitting method may be the least square curve fitting method. For example, the grayscale feature of each step $G=-\ln(I/I_0)$ in the high-energy of dual-energy mode is calculated to form an array composed of the grayscale feature and the mass-thickness, i.e., [(G1,M1), (G2,M2), (G3,M3) . . . ]. This array is fitted by using the least square method to acquire the four mass-thickness attenuation curves for the typical materials.

Figure 4:
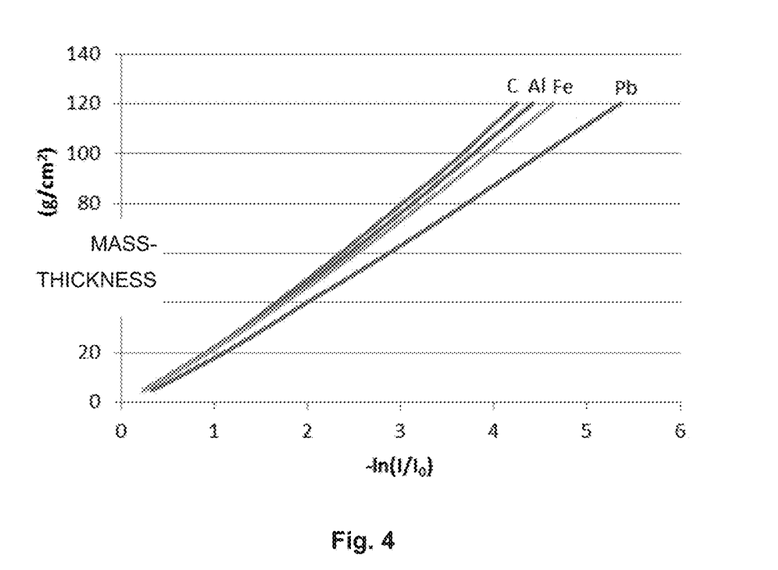
FIG. 4 is a diagram showing a mass-thickness curve acquired by using four calibration material blocks according to an embodiment of the present disclosure.

FIG. 4 is a diagram showing a mass-thickness curve acquired by using four calibration material blocks according to an embodiment of the present disclosure. As shown in FIG. 4, there are four mass attenuation curves for typical materials with the grayscale feature $-\ln(I/I_0)$ (i.e., the natural logarithm of the ratio between the value I of the X-ray after passing through a certain material and the value $I_0$ without any attenuation) as the abscissa and the mass-thickness as the ordinate in units of $g/cm^2$. The curves increase monotonically. From the upper left corner to the lower right corner, the atomic number is increased from small to large. The curves for graphite, aluminum, and iron are close to each other, and the curve for lead is rather far from the other curves.

Figure 5:
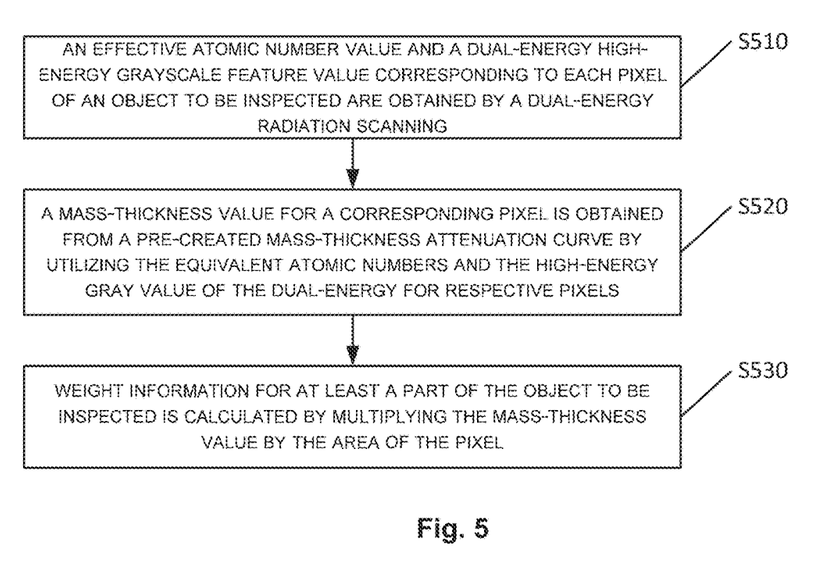
FIG. 5 is a flow chart describing a process of calculating weight information for an object to be inspected in a dual-energy system according to an embodiment of the present disclosure.

FIG. 5 is a flow chart describing a process of calculating weight information for an object to be inspected in a dual-energy system according to an embodiment of the present disclosure.

As shown in FIG. 5, at the step S510, an effective atomic number value and a dual-energy high-energy grayscale feature value corresponding to each pixel of an object to be inspected 130 are obtained by a dual-energy radiation scanning. For example, after the X-ray source 110 emits the X-ray beam in the dual-energy mode to acquire the image of the object to be inspected 130, the image is first corrected and its material is identified, and then the effective atomic number value Z of material corresponding to each pixel is acquired. After that, the high-energy gray value of the dual-energy for each pixel $G=-\ln(I/I_0)$ is calculated, and the position of (G, Z) is located on the mass-thickness attenuation curve. Since four points $(G, Z_6)$, $(G, Z_{13})$, $(G, Z_{26})$, and $(G, Z_{82})$ are known, and the mass-thickness attenuation curve increase monotonically, (G, Z) is compared with the above four points to determine that (G, Z) is equal to one of them or located between two of the known points. If it is equal to one of them, then the mass-thickness value M may be acquired directly; and if it is located between two of the known points, then it is linearly interpolated to acquire the corresponding mass-thickness value M.

At the step S520, a mass-thickness value for a corresponding pixel is obtained from a pre-created mass-thickness attenuation curve by utilizing the effective atomic numbers and the high-energy gray value of the dual-energy for respective pixels. For example, after the X-ray source 110 emits the X-ray beam in the dual-energy mode to acquire the image of the object to be inspected, the image is first corrected and its material is identified, and then the effective atomic number value Z of material corresponding to each pixel is acquired. After that, the grayscale feature of each pixel $G=-\ln(I/I_0)$ in the high-energy of the dual-energy mode is calculated, and the position of (G, Z) is located on the mass-thickness attenuation curve to acquire the corresponding mass-thickness value M.

At the step S530, weight information for at least a part of the object to be inspected 130 is calculated by multiplying the mass-thickness value by the area of the pixel. In an embodiment of the present application, a physical dimension $d1=P*D_{so}/D_{sd}$ corresponding to each pixel on an X-ray image in a direction in which detectors are arranged may be estimated based on a pitch P between detector pixels, a distance $D_{sd}$ between an X-ray source (abbreviated as s) and the detectors (abbreviated as d), and a distance $D_{so}$ between the X-ray source and the object to be inspected (abbreviated as o). It is to be noted that typically the object to be inspected 130 has a certain thickness, and the distance from the X-ray source to the object may be equivalent to the distance from the X-ray source to the center of the object. The value of the scanning speed divided by the detector acquiring frequency is calculated to acquire the pixel physical dimension d2 in the scanning direction where the scanning speed is the speed of the object to be inspected 130 relative to the X-ray source. Thus, the area of each pixel $S=d1*d2$ is acquired.

For example, the weight $g=M*S$ of each pixel is calculated. The whole scanning image is traversed to accumulate the weight information for all the pixels such that the weight of the object to be inspected 130 is acquired, or an ROI (Region of Interest) is selected by a mouse on the software interface which displays images, such that the weight of all the pixels within this region is accumulated to acquire the weight information for the ROI.

The method according to the above embodiments may be applied to a single-energy imaging process in which only the mass-thickness attenuation curve is used and the classification curve is not used. There is only one (not four) mass-thickness attenuation curve. The single-energy system cannot acquire the material properties of the object to be inspected 130, and therefore when it is calibrated, it is sufficient to use one moderate typical material. Since the mass attenuation curves for organics, mixture, and inorganics are close to each other, and the heavy metal differs from these three materials greatly, and heavy metal is rare and organics, mixture, and inorganics are common in a typical scanning, a moderate mixture of aluminum may be selected in calibration to acquire a single mass-thickness attenuation curve.

Figure 6:
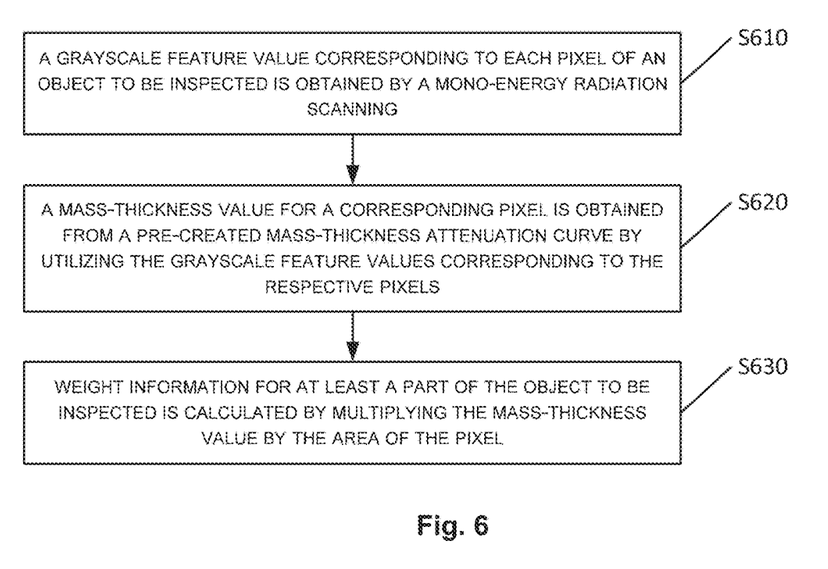
FIG. 6 is a flow chart describing a process of calculating weight information for an object to be inspected in a single-energy system according to an embodiment of the present disclosure.

FIG. 6 is a flow chart describing a process of calculating weight information for an object to be inspected 130 in a single-energy system according to an embodiment of the present disclosure.

As shown in FIG. 6, at the step S610, a grayscale feature value corresponding to each pixel of an object to be inspected 130 is obtained by a single-energy radiation scanning. For example, when the object to be inspected 130 is scanned, the grayscale feature $-\ln(I/I_0)$ of each pixel is acquired.

At the step S620, a mass-thickness value for a corresponding pixel is obtained from a pre-created mass-thickness attenuation curve by utilizing the grayscale feature values corresponding to the respective pixels. For example, the position of the grayscale feature $-\ln(I/I_0)$ is located on the mass-thickness attenuation curve to acquire the mass-thickness value.

At the step S630, weight information for at least a part of the object to be inspected 130 is calculated by multiplying the mass-thickness value by the area of the pixel. For example, likewise, the area of each pixel is calculated and therefore the product of the pixel area and the mass-thickness, i.e., the weight information is acquired. The whole scanning image is traversed to accumulate the weight for all the pixels such that the weight of the object to be inspected 130 is acquired, or an ROI is specified, such that the weight of all the pixels within this region is accumulated to acquire the weight information for the ROI.

Further, the method according to the embodiments of the present disclosure may be applied to a low-energy real/dummy dual-energy system (Kilo-electron Volts, or KeV, and Mega-electron Volts, or Mev are used typically). These two units are used to determine whether it is a low-energy or a high energy system (a system with dozens of KeVs—hundreds of KeVs is a low-energy system, and a system with several MeVs or above is a high-energy system). Since a low-energy real/dummy dual-energy system does not have a capability to recognize the heavy metal, the typical material "lead" may be omitted when the calibration device is designed, and only the typical materials, "graphite", "aluminum", and "iron" for organics, mixture, and inorganics are used. The thickness and number of the steps can be determined based on the material recognition scope of the low-energy dummy dual-energy system. The high-energy real dual-energy system has the capability of recognizing organics, mixture, inorganics, and heavy metal, and therefore four types of calibration materials may be selected, i.e. Graphite, aluminum, iron, and lead. Likewise, the thickness and number of the steps can be determined based on the material recognition scope of the low-energy dummy dual-energy system. Of course, in a low-energy single-energy and/or high-energy single-energy system, the above method according to the embodiments of the present disclosure may also be applicable.

The above detailed description has already set forth numerous embodiments of the method and device for estimating the weight information of the object to be inspected 130 with reference to the diagrams, flow charts, and/or examples. In the case where the diagrams, flow charts, and/or examples comprise one or more functions and/or operations, one skilled in the art should appreciate that each function and/or operation in the diagrams, flow charts, or examples may be implemented by various structures, hardware, software, firmware or any combination thereof either alone and/or in any combination. In an embodiment, several parts of the subject matter described in the embodiments of the present disclosure may be implemented by Application Specific Integrated Circuit (ASIC), Field Programmable Gate Array (FPGA), Digital Signal Processor (DSP), or any other integrated form. However, one skilled in the art should appreciate that some aspects of the embodiment disclosed herein may be partially or wholly implemented in an integrated circuit equivalently, implemented as one or more computer programs running on one or more computers (for example, one or more programs running on one or more computer systems), implemented as one or more programs running on one or more processors (for example, one or more programs running on one or more micro-processors), implemented as firmware, or substantially any combination thereof, and one skilled in the art is capable to design the circuit and/or write software and/or firmware code. Further, one skilled in the art would appreciate that the mechanism of the subject matter of the present disclosure may be distributed in various forms of program products, and the exemplary embodiments of the subject matter of the present disclosure may be applicable irrespective of the specific types of signal carrier media for distribution. Examples of the signal carrier media comprise but not limited to: a recordable medium such as floppy disk, hard drive, compact disk (CD), digital versatile disk (DVD), digital tape, computer memory, etc.; and a transmission medium, such as digital and/or analog communication medium (for example, optical fiber, waveguide, wired communication link, wireless communication link, etc.)

Although the present disclosure is already described with reference to several typical embodiments, it is to be appreciated that the terms used herein are illustrative and exemplary, rather than limiting. Since the present disclosure may be practice in multiple forms without departing from the spirit or essence, it is to be noted that the above embodiments are not limited to any previously described details and shall be interpreted broadly within the spirit and scope defined by the claims. Therefore, all changes and variations fall into the scope of the claims or their equivalents shall be embraced by the claims.

We claim:

1. A method for estimating a weight of an object to be inspected in an inspection system, comprising:
   obtaining an effective atomic number and a dual-energy high-energy grayscale feature value corresponding to each pixel of the object to be inspected by a dual-energy radiation scanning;
   obtaining a mass-thickness value for a corresponding pixel from a pre-created mass-thickness attenuation curve by utilizing the effective atomic number and the dual-energy high-energy grayscale feature value for respective pixels; and
   calculating weight information for at least a part of the object to be inspected by multiplying the mass-thickness value by an area of the pixel.

2. The method according to claim 1, further comprising:
   estimating a physical dimension corresponding to each pixel on an image of the object to be inspected in a direction in which detectors are arranged, based on a pitch between detector pixels, a distance between an X-ray source and the detectors, and a distance between the X-ray source and the object to be inspected;
   obtaining a pixel physical dimension in a scanning direction based on a scanning speed and an acquiring frequency of the detectors; and obtaining an area of each pixel by multiplying the physical dimension in the direction in which the detectors are arranged by the pixel physical dimension in the scanning direction.

3. The method according to claim 1, further comprising creating the pre-created mass-thickness attenuation curve by:
utilizing different types of calibration material blocks with known thicknesses to acquire a relationship curve among an X-ray attenuation coefficient, the effective atomic number, and the mass-thickness value, as the pre-created mass-thickness attenuation curve.

4. The method according to claim 1, wherein the obtaining a mass-thickness value for a corresponding pixel comprises acquiring the mass-thickness value corresponding to both of the effective atomic number and dual-energy high-energy grayscale feature value is acquired by linear interpolation.

5. The method according to claim 1, wherein the calculating weight information for at least a part of the object to be inspected comprises acquiring the weight information for a region of interest by accumulating weights of pixels within the region of interest when information of the region of interest selected by a user is received.

6. A device for estimating a weight of an object to be inspected in an inspection system, the device comprising:
one or more processors; and
a memory connected to the one or more processors and having one or more programs stored therein, which, when executed by the one or more processors, cause the one or more processors to be configured to:
obtain an effective atomic number and a dual-energy high-energy grayscale feature value corresponding to each pixel of the object to be inspected by a dual-energy radiation scanning;
obtain a mass-thickness value for a corresponding pixel from a pre-created mass-thickness attenuation curve by utilizing the effective atomic number and the dual-energy high-energy grayscale feature value for respective pixels; and
calculate weight information for at least a part of the object to be inspected by multiplying the mass-thickness value by an area of the pixel.

7. A method for estimating a weight of an object to be inspected in an inspection system, the method comprising:
obtaining a grayscale feature value corresponding to each pixel of an object to be inspected by a single-energy radiation scanning;
obtaining a mass-thickness value for a corresponding pixel from a pre-created mass-thickness attenuation curve by utilizing the grayscale feature value corresponding to respective pixels; and calculating weight information for at least a part of the object to be inspected by multiplying the mass-thickness value by an area of the pixel.

8. The method according to claim 7, further comprising:
estimating a physical dimension corresponding to each pixel on an image of the object to be inspected in a direction in which detectors are arranged, based on a pitch between detector pixels, a distance between a X-ray source and the detectors, and a distance between the X-ray source and the object to be inspected;
obtaining a pixel physical dimension in a scanning direction based on a scanning speed and an acquiring frequency of the detectors; and
obtaining an area of each pixel by multiplying the physical dimension in the direction in which the detectors are arranged by the pixel physical dimension in the scanning direction.

9. The method according to claim 7, further comprising creating the pre-created mass-thickness attenuation curve by:
utilizing a calibration material block with a known thickness to acquire a relationship curve among an X-ray attenuation coefficient and the mass-thickness value, as the pre-created mass-thickness attenuation curve.

10. The method according to claim 7, further comprising selecting aluminum as a calibration material block to acquire the pre-created mass-thickness attenuation curve.

11. The method according to claim 7, wherein the calculating weight information for at least a part of the object to be inspected comprises acquiring the weight information for a region of interest by accumulating weights of pixels within the region of interest when information of the region of interest selected by a user is received.

12. A device for estimating a weight of an object to be inspected in an inspection system, the device comprising:
one or more processors; and
a memory connected to the one or more processors and having one or more programs stored therein, which, when executed by the one or more processors, cause the one or more processors to be configured to:
obtain a grayscale feature value corresponding to each pixel of an object to be inspected by a single-energy radiation scanning;
obtain a mass-thickness value for a corresponding pixel from a pre-created mass-thickness attenuation curve by utilizing the grayscale feature value corresponding to respective pixels; and
calculate weight information for at least a part of the object to be inspected by multiplying the mass-thickness value by an area of the pixel.

* * * * *